(12) United States Patent
Maertens et al.

(10) Patent No.: US 10,287,254 B2
(45) Date of Patent: May 14, 2019

(54) SALTS OF A DIHYDROQUINAZOLINE DERIVATIVE

(71) Applicant: AiCuris GmbH & Co. KG, Wuppertal (DE)

(72) Inventors: Welljanne Maertens, Dresden (DE); Christian Schickaneder, Dresden (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 15/338,984

(22) Filed: Oct. 31, 2016

(65) Prior Publication Data

US 2017/0114026 A1   Apr. 27, 2017

Related U.S. Application Data

(62) Division of application No. 14/381,625, filed as application No. PCT/EP2013/054109 on Feb. 28, 2013, now Pat. No. 9,512,085.

(30) Foreign Application Priority Data

Feb. 29, 2012   (DE) ........................ 10 2012 101 673

(51) Int. Cl.
  *C07C 309/29*   (2006.01)
  *C07C 309/30*   (2006.01)
  *C07D 239/84*   (2006.01)
  *A61K 31/517*   (2006.01)

(52) U.S. Cl.
  CPC .......... *C07D 239/84* (2013.01); *C07C 309/29* (2013.01); *C07C 309/30* (2013.01)

(58) Field of Classification Search
  CPC .... C07D 239/84; C07C 309/30; C07C 309/29
  See application file for complete search history.

(56) References Cited

U.S. PATENT DOCUMENTS

| | | | |
|---|---|---|---|
| 7,196,086 B2 * | 3/2007 | Wunberg | ............. C07D 239/84 514/252.17 |
| 8,084,604 B2 | 12/2011 | Gooβen | |
| 8,314,113 B2 | 11/2012 | Wunberg | |
| 8,513,255 B2 | 8/2013 | Wunberg | |
| 9,458,433 B2 | 10/2016 | Lischka | |
| 9,512,085 B2 | 12/2016 | Maertens | |
| 9,637,459 B2 | 5/2017 | Grunenberg | |
| RE46,791 E | 4/2018 | Wunberg | |
| 2005/0065160 A1 | 3/2005 | Wunberg et al. | |
| 2007/0191387 A1 | 8/2007 | Wunberg | |
| 2009/0221822 A1 | 9/2009 | Goossen | |
| 2016/0145216 A1 | 5/2016 | Schwab | |

FOREIGN PATENT DOCUMENTS

WO   2004/096778 A1   11/2004

OTHER PUBLICATIONS

International Search Report dated May 31, 2013 issued in corresponding PCT/EP2013/054109 application (pp. 1-2).
Non-final rejection in corresponding U.S. Appl. No. 15/640,661 dated Jul. 27, 2018 (pp. 1-18).

* cited by examiner

*Primary Examiner* — Amanda L Aguirre
(74) *Attorney, Agent, or Firm* — Millen White Zelano & Branigan

(57) ABSTRACT

The invention relates to besylate and tosylate salts of {8-fluoro-2-[4-(3-methoxyphenyl)piperazin-1-yl]-3-[2-methoxy-5-(trifluoromethyl)phenyl]-3,4-dihydroquinazolin-4-yl}acetic acid and solvates thereof, to the use thereof in a method of treating and/or preventing virus infections, and to the use thereof to produce drugs for use in treating and/or preventing diseases, in particular use as antiviral agents, in particular against cytomegaloviruses (FIG. 1).

9 Claims, 6 Drawing Sheets

Fig. 3:

XLIII

| peak name | retention time | relative area percent (with RF) % |
|---|---|---|
| non-specific impurities | 31.26 | 0.01 |
| quinazolyl piperazine | 35.23 | 0.04 |
| Total amount of impurities | --- | 0.05 |

Fig. 5:

XLV

| peak name | retention time | relative area percent (with RF) % |
|---|---|---|
| non-specific impurities | 31.30 | 0.01 |
| quinazolyl piperazine | 35.22 | 0.06 |
| quinazolyl dipiperazine | 43.79 | 0.01 |
| Total amount of impurities | — | 0.08 |

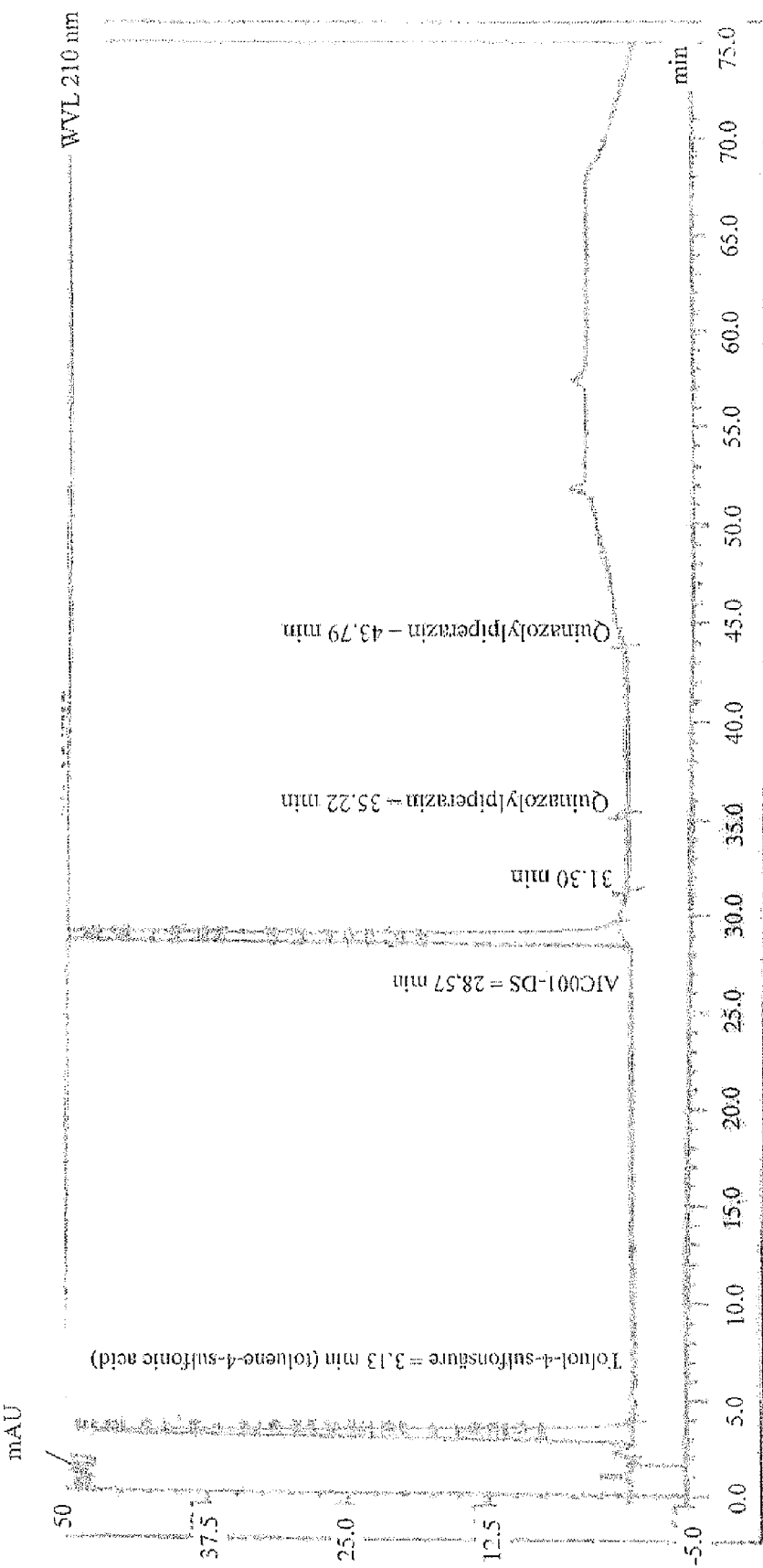

SALTS OF A DIHYDROQUINAZOLINE DERIVATIVE

The present invention relates to salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid and solvates thereof.

The invention further relates to methods for the production thereof, to the use thereof in methods of treating and/or preventing diseases, in particular virus infections, as well as to the use thereof for the production of drugs for use in methods of treating and/or preventing virus infections, in particular for methods of treating and/or preventing cytomegalovirus infections or infections with another representative of the Herpes viridae group.

{8-fluoro-2-[4-(3-methoxyphenyl)piperazine-1-yl]-3-[2-methoxy-5-(trifluoromethyl)-phenyl]-3,4-dihydroquinazoline-4-yl}acetic acid is known, for example, from WO 2004/096778, full disclosure of which is included herein by reference; it was developed by Applicant as a promising candidate for an antivirally active substance, in particular for combating infections caused by the human cytomegalovirus (HCMV). In the development process, however, it has proven to be extremely complicated to obtain the compound in crystalline form, whether as a zwitterion or in the form of a salt, and to date development has been carried out using the zwitterion in amorphous form. In particular for the purification of the active ingredient, but also for the use thereof in drugs, it would be desirable to obtain crystalline salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that can be produced easily and with a high yield.

One object of the invention is therefore to describe salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid with which crystalline products can be obtained. In particular, these crystalline products should feature a high level of purity and easy producibility. It would be especially favorable if products could be obtained that are largely or completely free of solvents.

Surprisingly, it has recently been discovered that {8-fluoro-2-[4-(3-methoxyphenyl)piperazine-1-yl]-3-[2-methoxy-5-(trifluoromethyl)phenyl]-3,4-dihydroquinazoline-4-yl}acetic acid will form well-defined crystalline salts with besylate and tosylate anions. It has further been discovered that these salts can be easily produced with a high level of purity and that they crystallize solvent-free.

The subject matter of this invention thus involves the crystalline besylate salts and crystalline tosylate salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid and solvates thereof.

Within the scope of the invention, besylate and tosylate salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid are adducts of a reaction of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid with benzenesulfonic acid or toluenesulfonic acid. The {8-fluoro-2-[4-(3-methoxyphenyl)piperazine-1-yl]-3-[2-methoxy-5-(trifluoromethyl)phenyl]-3,4-dihydroquinazoline-4-yl}acetic acid and the besylate or tosylate counterions may hereby be present in any ratio. However, an integer ratio is preferred (e.g. 1:1, 1:2, 1:3, 3:1, 2:1). The salts can thus be produced by means of a direct reaction of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid with benzenesulfonic acid or toluenesulfonic acid or by producing another acid salt of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid followed by exchange of the counterion.

The term "crystalline product" in the context of the present invention refers to S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate and S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate which, under X-ray diffraction analysis, exhibit the characteristic peak pattern as shown in FIGS. 1 and 2 or a similar peak pattern.

The terms "high purity, purity and pure" in connection with the S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate and the S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate according to the invention denote the presence thereof as a substance in a mixture of substances with a total content of <0.1%, preferably <0.08%, and most preferred <0.05% of the known impurities thereof of di-p-toluoyl-D-tartaric acid and/or S-quinazoline piperazine, and/or quinazoline ethyl ester and/or quinazoline dipiperazine and/or non-specific impurities thereof when measured by means of HPLC according to Method 4 (see exemplary embodiments C.).

Within the scope of the invention, the term "solvates" refers to those forms of the salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which form a complex through coordination with solvent molecules. Hydrates are a special form of solvates in which the coordination takes place with water.

Within the scope of the present invention, the monobesylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is preferred. Further preferred within the scope of the invention is the monotosylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid.

Further preferred within the scope of the invention is a besylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that shows characteristic peaks at about 6.9, 10.1 and 22.2 degrees 2theta in the X-ray powder diffractogram (XRD).

Also preferred within the scope of this invention is a tosylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that shows characteristic peaks at about 6.9 and 20.7 degrees 2theta in the X-ray powder diffractogram (XRD).

As is readily apparent to a person skilled in the art, {8-fluoro-2-[4-(3-methoxyphenyl)piperazine-1-yl]-3-[2-methoxy-5-(trifluoromethyl)phenyl]-3,4-dihydroquinazoline-4-yl}acetic acid possesses a stereocentre at the carbon in the 4-position in the dihydroquinazoline ring. Within the scope of the present invention, it is particularly preferred if this carbon possesses the S-configuration.

The salts according to the invention are generally produced by reacting {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a basic salt thereof with benzenesulfonic acid or toluenesulfonic acid in a solvent.

The term "easy production" in the context of the invention refers to obtaining crystalline products of S(+)-{8-fluoro-2-[4-(3-methoxyphenyl)piperazine-1-yl]-3-[2-methoxy-5-(trifluoromethyl)phenyl]-3,4-dihydroquinazoline-4-yl)acetic acid besylate and S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate by means of the above-described reaction of (+)-(8-fluoro-2-[4-(3-methoxyphenyl)piperazine-1-yl]-3-[2-methoxy-5-(trifluoromethyl)phenyl]-3,4-dihydroquinazoline-4-yl}acetic acid or a basic salt thereof with proportionate amounts of benzenesulfonic acid or toluenesulfonic acid in a solvent.

It is further possible to react an acid salt of (+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid that is not a besylate or tosylate salt with a source for besylate or tosylate anions in a solvent.

In particular, the above-mentioned reactions involve the use of a mixture of water and at least one ($C_3$-$C_6$) alkanone as solvent.

The subject matter of the invention thus also includes a method for the production of a besylate salt or tosylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid using the following steps:

a.) Dissolving {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a solvate thereof in a mixture of water and at least one ($C_3$-$C_6$) alkanone, if necessary under heat.
b.) Adding benzenesulfonic acid or toluenesulfonic acid to the solution obtained in step a.),
c.) Cooling down the solution obtained in step b.) in order to initiate the crystallization of the salt or of a solvate of the salt,
d.) Separating the crystallized-out salt or solvate thereof obtained in step c.), and
e.) Drying the salt or solvate obtained in step d.).

The salts according to the invention thus obtained can, if necessary, be further processed, e.g. recrystallized or micronized, in order to further adjust their physical properties to the intended use.

The salts according to the invention are also preferably used for purifying {8-fluoro-2-[4-(3-methoxyphenyl)piperazine-1-yl]-3-[2-methoxy-5-(trifluoromethyl)phenyl]-3,4-dihydroquinazoline-4-yl}acetic acid. For this purpose, the {8-fluoro-2-[4-(3-methoxyphenyl)piperazine-1-yl]-3-[2-methoxy-5-(trifluoromethyl)phenyl]-3,4-dihydroquinazoline-4-yl}acetic acid to be purified reacts in a solvent with benzenesulfonic acid or toluenesulfonic acid, the resulting crystalline salt is isolated and the zwitterionic form of the {8-fluoro-2-[4-(3-methoxyphenyl)piperazine-1-yl]-3-[2-methoxy-5-(trifluoro-methyl)phenyl]-3,4-dihydroquinazoline-4-yl}acetic acid is released again by treating the salt with a buffer solution at a pH in the range of 5 to 7.

The subject matter of the invention is also a method for purifying {8-fluoro-2-[4-(3-methoxyphenyl)piperazine-1-yl]-3-[2-methoxy-5-(trifluoromethyl)phenyl]-3,4-dihydroquinazoline-4-yl}acetic acid using the following steps:

1.) Reacting {8-fluoro-2-[4-(3-methoxyphenyl)piperazine-1-yl]-3-[2-methoxy-5-(trifluoromethyl)phenyl]-3,4-dihydroquinazoline-4-yl}acetic acid in a solvent with benzenesulfonic acid or toluenesulfonic acid to obtain a crystalline salt,
2.) Isolating the salt obtained in step 1.),
3.) Treating the isolated salt obtained in step 2.) with a buffer solution at a pH in the range of 5 to 7 to release a zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, and
4.) Isolating the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid obtained in step 3.).

The {8-fluoro-2-[4-(3-methoxyphenyl)piperazine-1-yl]-3-[2-methoxy-5-(trifluoromethyl)-phenyl]-3,4-dihydroquinazoline-4-yl}acetic acid, which is used to produce the salts according to the invention, is known and can be produced, for example, by the method described in WO 2006/133822.

The production takes place in particular by the saponification of the ester of a compound having the formula (II)

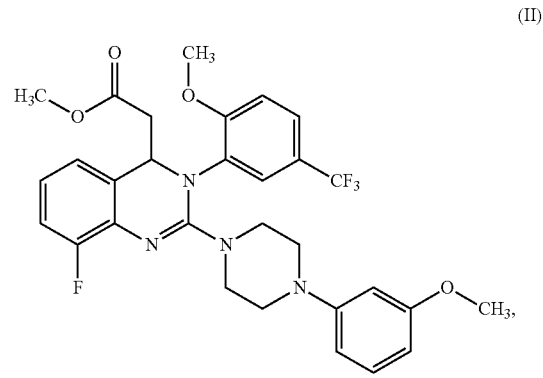 [SMILES: COC(=O)CC1c2cccc(F)c2N=C(N2CCN(c3cccc(OC)c3)CC2)N1c1cc(C(F)(F)F)ccc1OC]

(II)

with a base.

The compound having the formula (II) can be produced by reacting a compound having the formula (III)

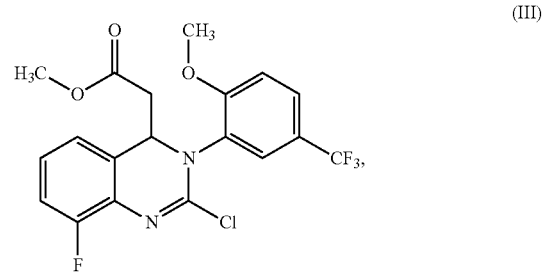 [SMILES: COC(=O)CC1c2cccc(F)c2N=C(Cl)N1c1cc(C(F)(F)F)ccc1OC]

(III)

with a compound having the formula (IV) in the presence of a base

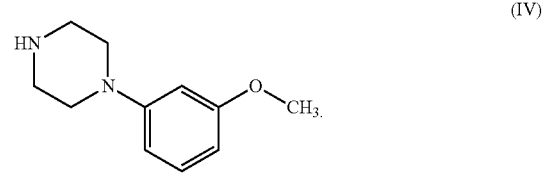 [SMILES: COc1cccc(N2CCNCC2)c1]

(IV)

The compound having the formula (III) can be produced by reacting a compound having the formula (V)

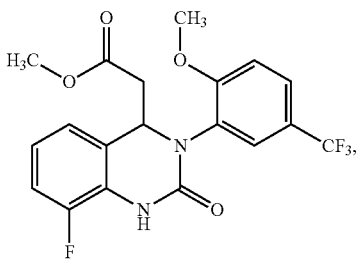

(V)

with phosphorus oxychloride, phosphorus trichloride or phosphorus pentachloride in the presence of a base.

The compound having the formula (V) can be produced by reacting a compound having the formula (VI)

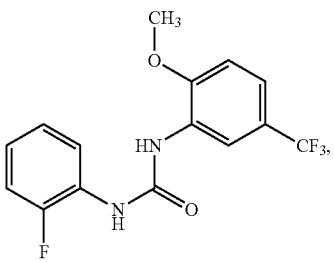

(VI)

in the first step with acrylic acid methyl ester in the presence of a palladium catalyst and oleum, and in the second step with a base.

Compounds having the formulae (IV) and (VI) are in principle known to a person skilled in the art or can be produced by customary methods known from the literature.

The saponification of the ester of a compound having the formula (II) to form {8-fluoro-2-[4-(3-methoxyphenyl)piperazine-1-yl]-3-[2-methoxy-5-(trifluoromethyl)phenyl]-3,4-dihydroquinazoline-4-yl}acetic acid is achieved by reacting a compound having the formula (I) with a base in an inert solvent, in a temperature range from 18° C. up to reflux of the solvent, preferably at 18 to 50° C., more preferably at 20 to 30° C., at normal pressure, within a period of, for example, 0.5 to 10 hours, preferably within 1 to 5 hours.

Bases are, for example, alkali hydroxides, such as sodium, lithium or potassium hydroxide, or alkali carbonates, such as cesium carbonate, sodium or potassium carbonate, or alcoholates such as sodium or potassium methanolate, or sodium or potassium ethanolate, where the base may be present in aqueous solution.

Inert solvents are, for example, ethers, such as 1,2-dimethoxyethane, methyl tert-butyl ether (MTBE), dioxane, tetrahydrofuran, glycol dimethyl ether or diethylene glycol dimethyl ether, alcohols such as methanol, ethanol, n-propanol, iso-propanol, n-butanol or tert-butanol, or water, or mixtures of solvents.

Sodium hydroxide in water and MTBE are preferred.

The synthesis of a compound having the formula (II) from a compound having the formula (III) and a compound having the formula (IV), in the presence of a base, takes place in an inert solvent, in a temperature range from 40° C. up to reflux of the solvent, preferably at reflux of the solvent, at normal pressure, within for example 2 to 48 hours, preferably within 4 to 12 hours.

Bases are, for example, amine bases such as 1,8-diazabicyclo[5.4.0]undec-7-ene (DBU), 1-(3-methoxyphenyl)piperazine or triethylamine, or other bases such as potassium tert-butylate.

Inert solvents are, for example, chlorobenzene or ethers such as 1,2 dimethoxyethane, dioxane, glycol dimethyl ether or diethylene glycol dimethyl ether.

DBU in dioxane is preferred.

The conversion of a compound having the formula (V) to a compound having the formula (III) takes place by reacting a compound having the formula (V) with phosphorus oxychloride, phosphorus trichloride or phosphorus pentachloride, with phosphorus oxychloride being preferred, in the presence of a base in an inert solvent, in a temperature range from 40° C. up to reflux of the solvent, preferably at reflux of the solvent, at normal pressure, within for example 1 to 48 hours, preferably within 2 to 12 hours.

Bases are, for example, amines such as 1,8-diazabicyclo[5.4.0]undec-7-ene (DBU), pyridine or triethylamine, or other bases such as potassium tert-butylate.

Inert solvents are for example hydrocarbons such as benzene, xylene, toluene or chlorobenzene.

DBU in chlorobenzene is preferred.

The conversion of a compound having the formula (VI) to a compound having the formula (V) takes place, in the first step, by reacting a compound of the formula (VI) with acrylic acid methyl ester in the presence of a palladium catalyst and oleum in a solvent, in a temperature range from 0° C. to 40° C., preferably at room temperature, and in the second step by reaction with a base in an inert solvent, in a temperature range from 40° C. up to reflux of the solvent, preferably at reflux of the solvent, at normal pressure, within for example 1 to 48 hours, preferably within 2 to 12 hours.

Palladium catalysts in the first step are, for example, palladium(II) acetate, bis(triphenylphosphine)palladium(II) chloride, tetrakis(triphenylphosphine)palladium(0), bis(tri(o-tolyl)phosphine)palladium-(II)-chloride, or a palladium catalyst produced from bis(acetonitrile)dichloropalladium or palladium(II) acetate and a ligand, for example tris(o-tolyl)phosphine, triphenylphosphine or diphenylphosphino ferrocene.

Solvents in the first step are, for example, organic acids such as acetic acid or propionic acid.

Palladium(II) acetate in acetic acid is preferred.

Bases in the second step are, for example, DBU, triethylamine or diisopropylethylamine.

Inert solvents in the second step are, for example, ethers such as 1,2-dimethoxyethane, dioxane, glycol dimethyl ether or diethylene glycol dimethyl ether, hydrocarbons such as benzene, xylene or toluene, or other solvents such as isobutyronitrile, acetonitrile, acetone, nitrobenzene, dimethylformamide, dimethylacetamide, dimethylsulfoxide or N-methylpyrrolidone.

DBU in acetone is preferred.

The production of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid used to produce the salts according to the invention is described in more detail, by way of example, in the following Synthesis Diagram 1. This synthesis diagram is nothing more than an example and should in no way be understood as restrictive.

Synthesis Diagram 1
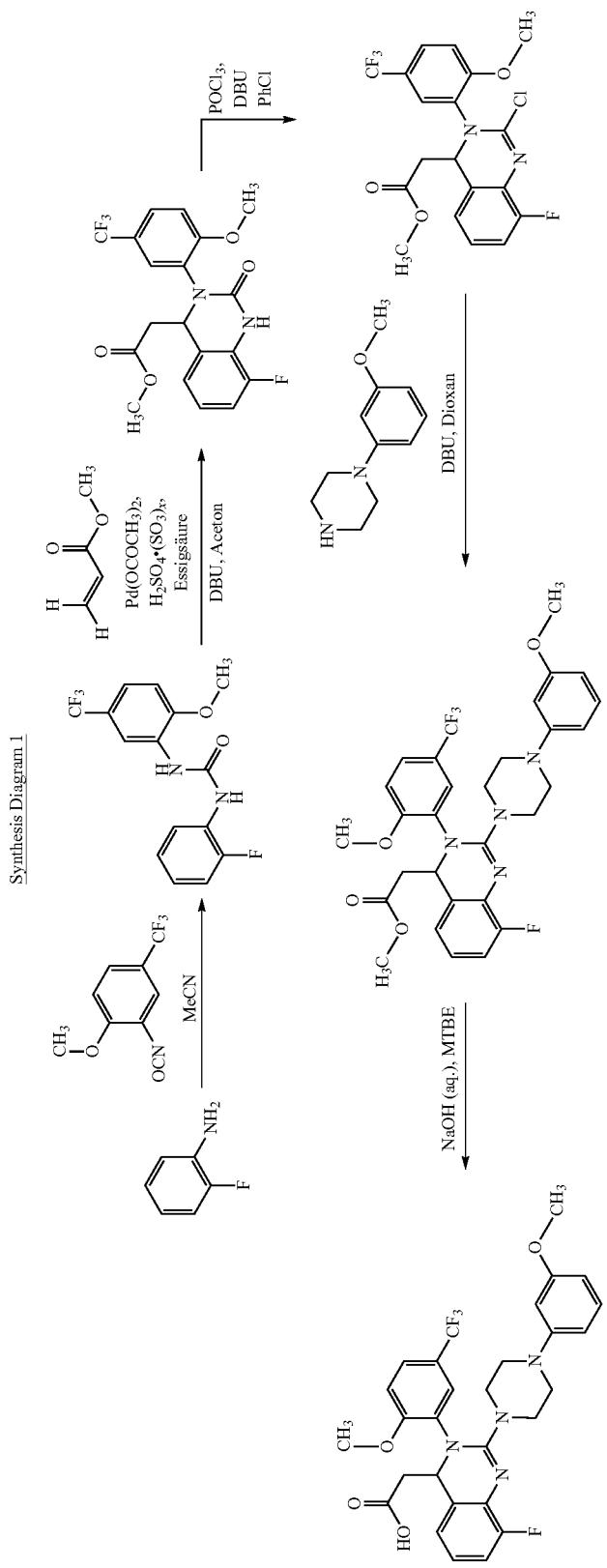
[Translation key: Essigsäure = acetic acid]

As already mentioned further above, the {8-fluoro-2-[4-(3-methoxyphenyl)piperazine-1-yl]-3-[2-methoxy-S-(trifluoromethyl)phenyl]-3,4-dihydroquinazoline-4-yl}acetic acid is used preferably in the form of the S-enantiomer. This S-enantiomer can be produced as shown, for example, in the following Synthesis Diagram 2.

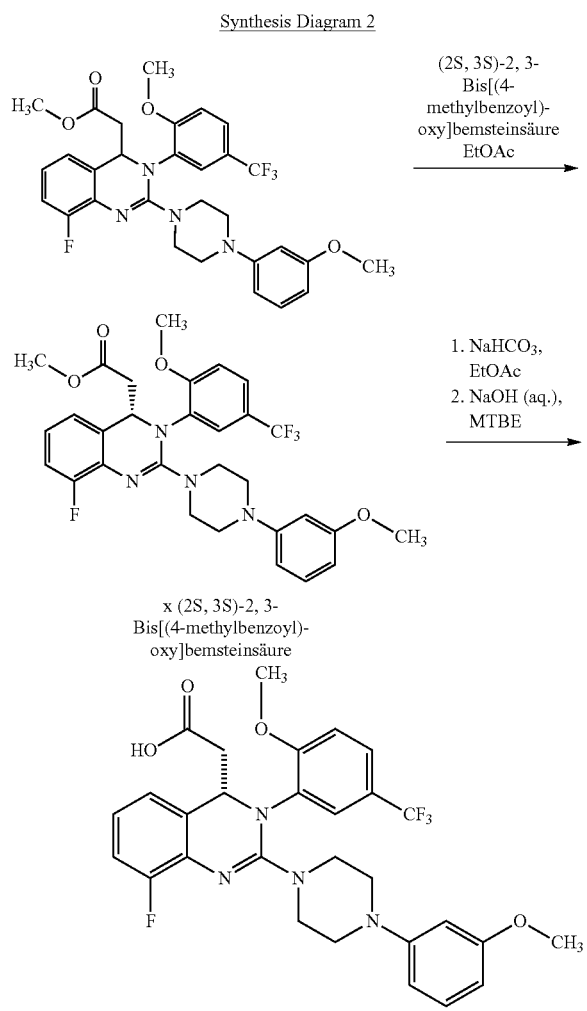

The salts according to the invention exhibit an antiviral effect against representatives of the Herpes viridae group (herpes viruses), above all against the cytomegaloviruses (CMV), in particular against the human cytomegalovirus (HCMV). They are thus suitable for methods of treating and/or preventing diseases, especially infections with viruses, in particular the viruses referred to herein and the infectious diseases caused by them.

The term "virus infection" is understood here to mean not only an infection with a virus but also a disease caused by infection with a virus.

Due to their properties and characteristics the salts according to the invention can be used to produce drugs that are suitable for use in methods of preventing and/or treating diseases, in particular virus infections.

The following areas of indication can be mentioned, by way of example:
1) Treatment and prevention of HCMV infections in AIDS patients (retinitis, pneumonitis, gastrointestinal infections).
2) Treatment and prevention of cytomegalovirus infections in bone marrow and organ transplant patients who often contract life-threatening HCMV pneumonitis or encephalitis, as well as gastrointestinal and systemic HCMV infections.
3) Treatment and prevention of HCMV infections in neonates and infants.
4) Treatment of acute HCMV infection in pregnant women.
5) Treatment of HCMV infection in immune-suppressed patients suffering from cancer and undergoing cancer therapy.
6) Treatment of HCMV-positive cancer patients with the aim of reducing HCMV-mediated tumour progression (cf. J. Cinatl, et al., FEMS Microbiology Reviews 2004, 28, 59-77).

The salts according to the invention are preferably used to produce drugs which are suitable for use in methods of preventing and/or treating infections with a representative of the Herpes viridae group, in particular a cytomegalovirus, in particular the human cytomegalovirus.

Due to their pharmacological properties and characteristics, the salts according to the invention can be used by themselves and, if needed, also in combination with other active substances, especially antiviral substances such as for example valganciclovir, ganciclovir, valacyclovir, acyclovir, foscarnet, cidofovir and related derivatives in methods of treating and/or preventing virus infections, in particular HCMV infections.

Further subject matter of the present invention is the use of the salts according to the invention in a method for treating and/or preventing diseases, preferably virus infections, in particular infections with the human cytomegalovirus (HCMV) or another representative of the Herpes viridae group.

Further subject matter of the present invention is the use of the salts according to the invention in methods of treating and/or preventing diseases, in particular the aforementioned diseases.

Further subject matter of the present invention is the use of the salts according to the invention to produce a drug for use in methods of treating and/or preventing diseases, in particular the aforementioned diseases.

Further subject matter of the present invention is a method for treating and/or preventing diseases, in particular the aforementioned diseases, using an antivirally effective amount of the salts according to the invention.

The salts according to the invention may be effective systemically and/or locally. For this purpose they may be administered in a suitable manner, such as orally, parenterally, pulmonally, nasally, sublingually, lingually, buccally, rectally, dermally, transdermally, conjunctivally, otically or as an implant or stent.

The salts according to the invention may be administered in suitable forms for these administration routes.

Means of administration that function according to the state of the art and that release the salts according to the invention quickly and/or in modified form are suitable for oral administration; said means of administration contain the compounds of the invention in crystalline and/or amorphized and/or dissolved form, such as tablets (uncoated or coated tablets, for example, with enteric-coating or with coatings that dissolve slowly or are insoluble, and which control the release of the compound of the invention), tablets or film-coated/wafer-like forms that dissolve quickly in the mouth, film-coated forms/lyophylisates, capsules (for example hard or soft gelatin capsules), sugar-coated tablets, granules, pellets, powders, emulsions, suspensions, aerosols or solutions.

Parenteral administration can be done by bypassing a resorption step (e.g., intravenous, intra-arterial, intracardiac, intraspinal or intralumbar) or by including resorption (e.g., intramuscular, subcutaneous, intracutaneous, percutaneous or intraperitoneal). For parenteral administration, suitable forms of administration include injection and infusion preparations in the form of solutions, suspensions, emulsions, lyophilisates or sterile powders.

For other routes of administration, for example inhalation drugs (inter alia powder inhalers, nebulizers), nose drops, nose solutions, nose sprays are suitable as well as lingually, sublingually or buccally administered tablets, film-coated/wafer-like medications or capsules, suppositories, ear or eye preparations, vaginal capsules, aqueous suspensions (lotions, shaking mixtures), lipophilic suspensions, ointments, creams, transdermal therapeutic systems, milk, pastes, foams, dusting powders, implants or stents.

The salts according to the invention can be transferred into the indicated application forms. This can be done in a conventional manner by mixing with inert, non-toxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as ascorbic acid), dyes (e.g. inorganic pigments such as iron oxides) and taste and/or olfactory corrigents.

Another subject matter of the present invention includes drugs comprising at least one salt according to the invention, usually together with one or more inert, non-toxic, pharmaceutically suitable excipients, and the use thereof for the aforementioned purposes.

It has generally proven advantageous for oral applications to administer quantities of the pure active ingredient between 0.01 and 25 mg/kg, preferably about 0.1 to 10 mg/kg per body weight to achieve effective results.

Nevertheless, it may be necessary to deviate from the amounts mentioned, namely depending on body weight, administration route, individual response to the active substance, type of preparation and time or interval at which administration takes place. For example, in certain cases it may be sufficient to get by with less than the aforementioned minimum amount, while in other cases the stated upper limit has to be exceeded. When administering large amounts it may be recommendable to distribute these in several individual doses over the course of a day.

It goes without saying that the features mentioned above and those yet to be explained may not only be used in the individually indicated combinations, but also in other combinations or in isolation, without departing from the scope of the invention.

In the following, the invention will be described in more detail based on examples and with reference to the enclosed drawings, which show in:

BRIEF DESCRIPTION OF THE FIGURES

FIG. 3 an HPLC analysis of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate by means of the relative area percent method including the respective response factors (RF); peak name, retention time, relative area percent (with RF) % in table form.

FIG. 5 an HPLC analysis of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate by means of the relative area percent method including the respective response factors (RF); peak name, retention time, relative area percent (with RF) % in table form.

FIG. 6 an HPLC purity chromatogram of S(+){8-fluoro-2-[4-(3-methoxyphenyl)piperazine-1-yl]-3-[2-methoxy-5-(trifluoromethyl)phenyl]-3,4-dihydroquinazoline-4-yl})acetic acid tosylate.

Figure 1:
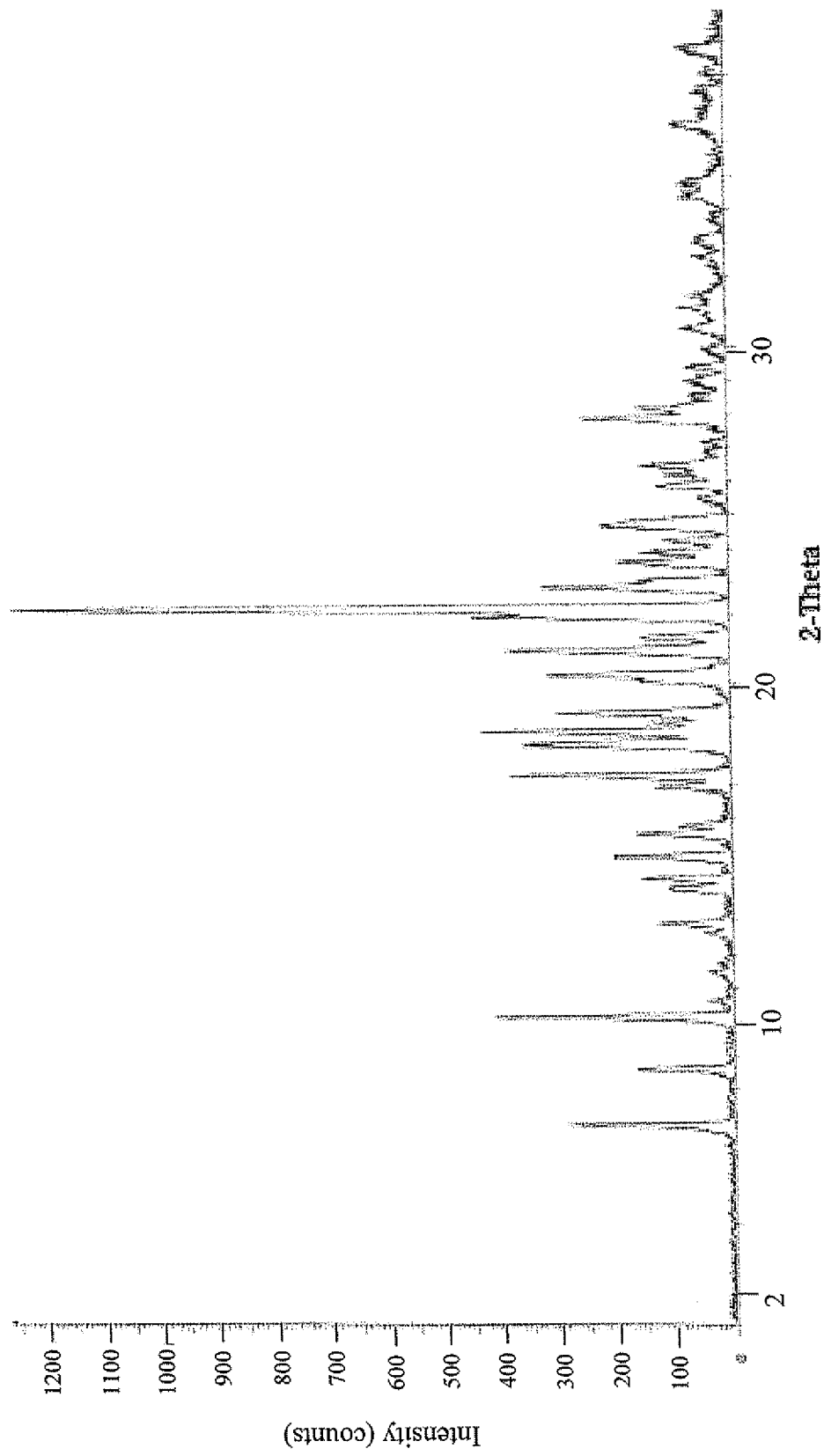
FIG. 1 an X-ray powder diffractogram (XRD) of a besylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that was produced according to Example 1; and in FIG. 2 an X-ray powder diffractogram (XRD) of a tosylate salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that was produced according to Example 2.

Unless indicated otherwise, the percentages given in the following tests and examples are weight percentages, parts are weight proportions. Solvent ratios, dilution ratios and concentrations of liquid solutions relate, in each case, to the volume.

List of Abbreviations

ACN Acetonitrile
API active pharmaceutical ingredient
API-ES-pos. Atmospheric pressure ionization, electrospray, positive (in MS)
API-ES-neg. Atmospheric pressure ionization, electrospray, negative (in MS)
ca. circa
CI, $NH_3$ chemical ionization (with ammonia)
DBU 1,8-Diazabicyclo[5.4.0]undec-7-en
DMAP 4-(Dimethylamino)pyridine
DMSO Dimethyl sulfoxide
ESTD external standardization
h hour(s)
HPLC high pressure liquid chromatography
conc. concentrated
min. minutes
MS mass spectroscopy
MTBE Methyl tert-butylether
NMR nuclear magnetic resonance spectroscopy
$R_T$ retention time (in HPLC)
VTS vacuum drying cabinet General HPLC Methods:

Method 1 (HPLC): Instrument: HP 1050 with variable wavelength detection; column: Phenomenex Prodigy ODS (3) 100 A, 150 mm×3 mm, 3 μm; Eluent A: (1.0 g KH2PO4+ 1.0 ml H3PO4)/1 water, Eluent B: acetonitrile; gradient: 0 min 10% B, 25 min 80% B, 35 min 80% B; flow: 0.5 ml/min; temp.: 45° C.; UV detection: 210 nm.

Method 2 (HPLC): Instrument: HP 1050 with variable wavelength detection; column: Chiral AD-H, 250 mm×4.6 mm, 5 m; Eluent A: n-heptane+0.2% diethylamine, Eluent B: isopropanol+0.2% diethylamine; gradient: 0 min 12.5% B, 30 min 12.5% B; flow: 1 ml/min; temp.: 25° C.; UV detection: 250 nm.

Method 3 (HPLC): Instrument: HP 1050 with variable wavelength detection; column: Chiral AD-H, 250 mm×4.6 mm, 5 μm; Eluent A: n-heptane+0.2% diethylamine, Eluent B: isopropanol+0.2% diethylamine; gradient: 0 min 25% B, 15 min 25% B; flow: 1 ml/min; temp.: 30° C.; UV detection: 250 nm.

EXAMPLES

A.) Production of {8-fluoro-2-[4-(3-methoxyphenyl) piperazin-1-yl]-3-[2-methoxy-5-(trifluoromethyl) phenyl]-3,4-dihydroquinazoline-4-yl}acetic acid

Example 1A

N-(2-fluorophenyl)-N'-[2-methoxy-5-(trifluoromethyl)phenyl]urea

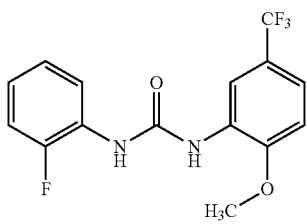 [SMILES: COc1ccc(C(F)(F)F)cc1NC(=O)Nc1ccccc1F]

2-methoxy-5-trifluoromethylphenyl isocyanate (78 kg) is melted at approx. 35° C. and dissolved in acetonitrile (a total of approx. 270 l), then 2-fluoroaniline (39.9 kg) is added and rinsed with acetonitrile (approx. 25 l). The resulting clear solution is agitated for 4 h at reflux and then cooled to approx. 75° C. Once this temperature is reached, the solution is inoculated with seed crystals of the desired end product (200 g), agitated for an additional 15 min., and then cooled to 0° C. over the course of 3 h. The resulting crystalline product is isolated by centrifugation, washed with cold acetonitrile (twice using approx. 13 l), and dried at 45° C. in the VTS under purging with nitrogen (approx. 3.5 h). A total of 101.5 kg of N-(2-fluorophenyl)-N'-[2-methoxy-5-(trifluormethyl)phenyl]urea is thus obtained as a solid, corresponding to 85.9% of theory.

$^1$H NMR (300 MHz, d$_6$-DMSO): δ=8.93 (s, 1H), 8.84 (s, 1H), 8.52 (d, $^3$J=2, 3, 2H), 7.55 (d, $^2$J=7.7, 1H), 7.38-7.26 (m, 3H), 7.22 (d, $^2$J=8.5, 1H), 4.00 (s, 3H) ppm;

MS (API-ES-pos.): m/z=409 [(M+H)$^+$, 100%];

HPLC (Method 1): R$_T$=22.4 and 30.6 min.

Example 2A

Methyl-(2Z)-3-[3-fluoro-2-({[2-methoxy-5-(trifluoromethyl)phenyl]carbamoyl}amino)-phenyl]acrylate

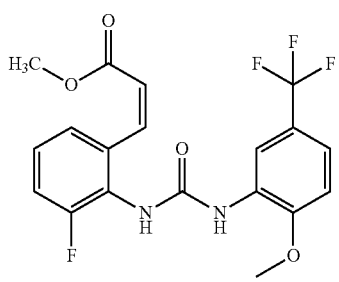 [SMILES: COC(=O)/C=C\c1cccc(F)c1NC(=O)Nc1cc(C(F)(F)F)ccc1OC]

N-(2-fluorophenyl)-N'-[2-methoxy-5-(trifluoromethyl) phenyl] urea (51 kg) is dissolved in acetic acid (approx. 430 l) in one reactor in a nitrogen atmosphere. Methyl acrylate (20.1 kg) is added to the resulting solution and the resulting suspension is agitated until further use. Acetic acid (950 l) is placed in a second reactor, oleum (57 kg) is carefully added and palladium (II) acetate (7 kg) is dissolved in the mixture. The suspension formed in the first reactor is then added to the mixture contained in the second reactor over the course of approx. 2 h; the reaction mixture is overflowed with a mixture of 96% nitrogen and 4% oxygen and the resulting reaction mixture is agitated for approx. 18 h at room temperature. Part of the acetic acid (approx. 900 l) is then distilled off; water (approx. 500 l) is added to the remaining reaction mixture over the course of approx. 1 h and the resulting suspension is agitated for 1 h. The resulting particulate matter is filtered off, washed once with a mixture of acetic acid and water (1:1) and twice with water, and finally dried at approx. 30 mbar and 50° C. A total of 44.8 kg of methyl-(2Z)-3-[3-fluoro-2-({[2-methoxy-5-(trifluoromethyl)phenyl]carbamoyl}amino)phenyl]acrylate is thus obtained as a solid, corresponding to 65.0% of theory.

$^1$H NMR (300 MHz, d$_6$-DMSO): δ=9.16 (s, 1H), 8.84 (s, 1H), 8.45 (d, 1.7 Hz, 1H), 7.73 (m, 2H), 7.33 (m, 3H), 7.22 (d, 8.6 Hz, 1H), 6.70 (d, 16 Hz, 1H), 3.99 (s, 3H), 3.71 (s, 3H) ppm;

MS (API-ES-pos.): m/z=429.9 [(M+NH$_4$)$^+$]; 412.9 [(M+H)$^+$]

HPLC: R$_T$=46.4 min.

Instrument: HP 1100 with variable wavelength detection; column: Phenomenex Prodigy ODS (3) 100 A, 150 mm×3 mm, 3 μm; Eluent A: (1.36 g KH$_2$PO$_4$+0.7 ml H$_3$PO$_4$)/1 of water, Eluent B: acetonitrile; gradient: 0 min 20% B, 40 min 45% B, 50 min 80% B, 65 min 80% B; flow: 0.5 ml/min; temp.: 55° C.; UV detection: 210 nm.

Example 3A

{8-fluoro-3-[2-methoxy-5-(trifluoromethyl)phenyl]-2-oxo-1,2,3,4-tetrahydroquinazoline-4-yl}methyl acetate

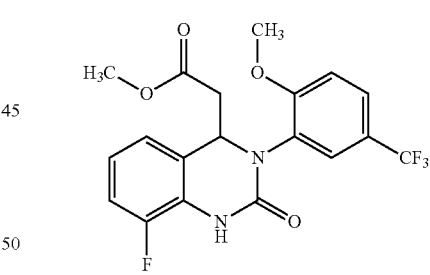

The compound in Example 2A (75 kg) is suspended in acetone (1600 l), and DBU (5.7 kg) is added. The resulting suspension is heated to reflux and agitated for 4 h at reflux. The resulting solution is cooled to a jacket temperature of 55° C. and filter through kieselguhr. Part of the solvent (approx. 1125 l) is removed by distillation and the remaining residue is cooled for 2 h to 0° C. The resulting solid is separated out by centrifugation, washed twice using cold acetone (approx. 15 l), and dried overnight at 45° C. under reduced pressure and under purging with nitrogen to constant mass. A total of 58.3 kg of {8-fluoro-3-[2-methoxy-5-(trifluoromethyl)phenyl]-2-oxo-1,2,3,4-tetrahydroquinazoline-4-yl} methyl acetate is thus obtained as a solid, corresponding to 84.1% of theory.

HPLC (Method 1): R$_T$=19.4 min.

Example 4A (2S,3S)-2,3-bis[(4-methylbenzoyl)oxy] succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}methyl acetate (1:1 salt) chlorination/amination/crystallization

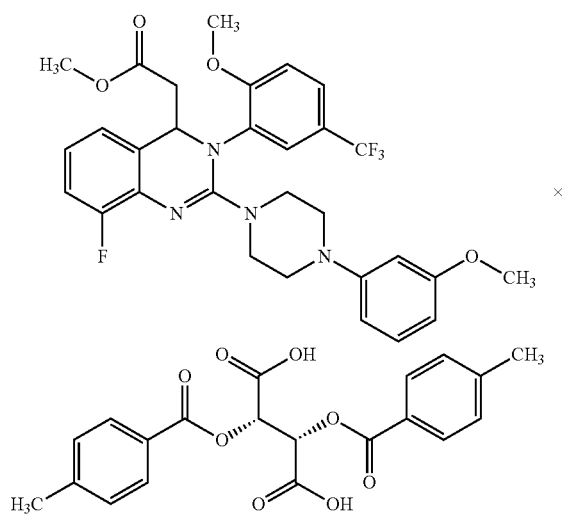

A solution of {8-fluoro-3-[2-methoxy-5-(trifluoromethyl)phenyl]-2-oxo-1,2,3,4-tetrahydroquinazoline-4-yl}methyl acetate (Example 3A, 129.2 kg) in chlorobenzene (800 l) is heated to reflux and azeotropically dried. Phosphorous oxychloride (144 kg) is added, and the reaction mixture is agitated for 3 h at reflux. Then, DBU (95 kg) and chlorobenzene (45 l) are added and agitated for additional 9 h at reflux. The reaction mixture is cooled to room temperature, hydrolyzed by adding water, diluted with chlorobenzene (80 l), and neutralized with an aqueous solution of ammonia (25%). The phases are separated, the organic phase is washed with water and the solvent is distilled off. The remaining residue is dissolved in dioxane (170 l). 3-methoxyphenylpiperazine (66 kg), DBU (52 kg), and an additional 90 l of dioxane are added and the reaction mixture is heated for 4 h at reflux. The reaction mixture is cooled to room temperature, added to ethyl acetate (1300 l), washed once with water, 3 times with 0.2 N HCl, and once with an aqueous solution of NaCl, and the solvent is distilled off. The resulting residue is dissolved in ethyl acetate (800 l) and added to a solution of (2S,3S)-2,3-bis[(4-methylbenzoyl)oxy] succinic acid (121 kg) in ethyl acetate (600 l). The resulting mixture is agitated for approx. 60 min. at room temperature and then inoculated with (2S,3S)-2,3-bis[(4-methylbenzoyl)oxy]-succinic acid-{(4S)-8-fluoro-2-[4-(3-methoxyphenyl)piperazine-1-yl]-3-[2-methoxy-5-(trifluoromethyl)-phenyl]-3,4-dihydroquinazoline-4-yl}methyl acetate and agitated for 3 days at room temperature. It is then cooled to 0-5° C. and agitated for an additional 3 h. The suspension is filtered and the remaining solid is rewashed in batches with ethyl acetate. A total of about 141 kg (calculated as dry weight) of the salt is thus obtained as a solid, corresponding to around 46.2% of theory, in three stages (chlorination, amination and crystallization) compared to the racemate).

$^1$H NMR (300 MHz, $d_6$-DMSO): δ=7.90 (d, $^2$J=7.8, 4H), 7.56 (d, $^2$J=8.3, 1H), 7.40 (d, 2J=7.8, 4H), 7.28-7.05 (m, 4H), 6.91-6.86 (m, 2H), 6.45 (d, 2J=8.3, 1H), 6.39-6.36 (m, 2H), 5.82 (s, 2H), 4.94 (m, 1H), 4.03 (q, $^2$J=7.1, 2H), 3.83 (brs, 3H), 3.69 (s, 3H), 3.64 (s, 3H), 3.47-3.36 (m, 8H and water, 2H), 2.98-2.81 (m, 5H), 2.58-2.52 (m, 1H), 2.41 (s, 6H), 1.99 (s, 3H), 1.18 (t, $^2$J=7.2, 3H) ppm;

HPLC (Method 1): $R_T$=16.6 and 18.5 min.

Example 5A (2S,3S)-2,3-bis[(4-methylbenzoyl)oxy] succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}methyl acetate (1:1 salt)/recrystallization (2S,3S)-2,3-bis[(4-methylbenzoyl)oxy] succinic acid—(S) {(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (141 kg, calculated as dry weight) is suspended in ethyl acetate (1400 l) and dissolved by heating to reflux (77° C.). The solution is filtered and slowly cooled to room temperature, which results in spontaneous crystallization. The suspension is agitated for 16 h at RT, and then cooled to 0-5° C. and agitated for additional 3 h. The suspension is filtered and the remaining solid is rewashed with cold ethyl acetate. The crystals are dried for 16 h in a vacuum at around 40° C. A total of 131.2 kg of the salt is obtained as a solid, corresponding to 93.0% of theory.

HPLC (Method 1): $R_T$=16.9 and 18.8 min.;
HPLC (Method 3): 99.9% e.e.

Example 6A (S)-{8-fluoro-2-[4-(3-methoxyphenyl)piperazine-1-yl]-3-(2-methoxy-5-trifluoromethyl-phenyl)-3,4-dihydroquinazoline-4-yl}acetic acid

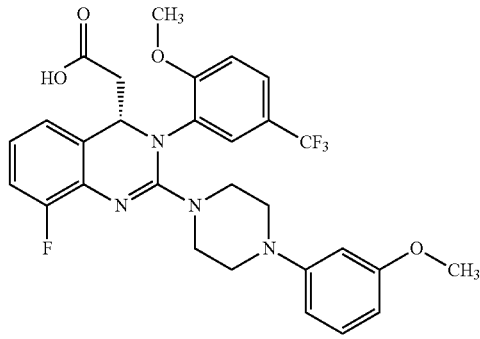 [SMILES: COc1cccc(N2CCN(C3=Nc4c(F)cccc4[C@H](CC(=O)O)N3c3cc(C(F)(F)F)ccc3OC)CC2)c1]

A mixture of (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (30.8 kg), sodium bicarbonate (16.4 kg), and water (315 l) is mixed with MTBE (160 l). The phases are separated and the organic phase is treated with 35 l of an approximately seven-percent aqueous solution of sodium bicarbonate. The phases are separated and the organic phase is added to 125 l of an approximately four-percent aqueous solution of sodium hydroxide. The reaction mixture is heated to reflux, the solution is evaporated to dryness, and the reactor contents are then agitated for an additional 5 h at 55-60° C. The reaction mixture is then added at approx. 22° C. to MTBE (160 l) and water (65 l) and agitated. The phases are separated and the organic phase is extracted with an approximately six-percent aqueous solution of sodium chloride (30 l). The combined aqueous phases are mixed with water (25 l) and MTBE (160 l) and the pH value is adjusted to approx. 6.5 with approx. 1 N of hydrochloric acid. The organic phase is separated, the solvent is evaporated to dryness, and the residue is dissolved in acetone (approx. 75 l). The solvent is changed to acetone (6 distillations with approx. 130 l each). The final product is then precipitated by adding water, isolated through centrifugation, and dried in a vacuum dryer. A total of 16.5 kg of (S)-{8-fluoro-2-[4-(3-methoxyphenyl)piperazine-1-yl]-3-(2-methoxy-5-trifluoromethylphenyl)-3,4-dihydroquinazoline-4-yl}acetic acid is thus obtained as an amorphous solid, corresponding to 96.4% of theory.

$^1$H NMR (300 MHz, d$_6$-DMSO): δ=7.53 (d, $^2$J=8.4, 1H), 7.41 (brs, 1H), 7.22 (d, $^2$J=8.5, 1H), 7.09-7.01 (m, 2H), 6.86 (m, 2H), 6.45 (dd, $^2$J=8.2, $^3$J=1.8, 1H), 6.39-6.34 (m, 2H), 4.87 (t, $^2$J=7.3, 1 H), 3.79 (brs, 3H), 3.68 (s, 3H), 3.50-3.38 (m, 4H), 2.96-2.75 (m, 5H), 2.45-2.40 (m, 1H) ppm;

MS (API-ES-neg.): m/z=571 [(M+H), 100%];
HPLC (Method 1): R$_T$=15.1 min;
HPLC (Method 2): 99.8% e.e.; Pd (ICP): <1 ppm.

B.) Exemplary Embodiments

Crystallization Experiments

Crystallization experiments to find a suitable crystalline salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid were conducted. The crystallization experiments were based on (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid and the respective acid either by slurrification in the individually specified solvent for one week at 20° C. or by crystallization through cooling/evaporation of a solution that was kept at 50° C. for 4 hours, followed by slow cooling to 20° C. at a ratio of 3° C./hour.

The results of the crystallization experiments are given in Table 1 below where the abbreviation API denotes (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid.

"API" is the acronym for "active pharmaceutical ingredient".

TABLE 1

Crystallization experiments using acid counterions

| Counterions | Ratio API:Counterions | Method | Solvent | Result (XRPD) |
|---|---|---|---|---|
| HCl | 1:2 | Cooling | Acetone, Acetonitrile, Methanol, THF | amorphous |
| | | Slurrification | Water, Acetonitrile, Methanol and Ethanol | |
| Citric acid | 1:1 | Cooling | Acetone, Acetonitrile, Methanol, THF | amorphous |
| | | Slurrification | Water, Acetonitrile Methanol and Ethanol | |
| Phosphoric acid | 1:1 | Cooling | Acetone, Acetonitrile, Methanol, THF | amorphous |
| | | Slurrification | Water, Acetonitrile, Methanol and Ethanol | |
| Gluconic acid | 1:1 | Cooling | Acetone, Acetonitrile, Methanol, THF | amorphous |
| | | Slurrification | Water, Acetonitrile Methanol and Ethanol | |
| Lactic acid | 1:1 | Cooling | Acetone, Acetonitrile, Methanol, THF | amorphous |
| | | Slurrification | Water, Acetonitrile Methanol and Ethanol | |
| Maleic acid | 1:1 | Cooling | Acetone, Acetonitrile, Methanol, THF | amorphous |
| | | Slurrification | Water, Acetonitrile Methanol and Ethanol | |
| Succinic acid | 1:1 | Cooling | Acetone, Acetonitrile, Methanol, THF | amorphous |
| | | Slurrification | Water, Acetonitrile Methanol and Ethanol | |
| Sulfuric acid | 1:1 | Cooling | Acetone, Acetonitrile, Methanol, THF | amorphous |
| | | Slurrification | Water, Acetonitrile Methanol and Ethanol | |
| Tartaric acid | 1:1 | Cooling | Acetone, Acetonitrile, Methanol, THF | amorphous |
| | | Slurrification | Water, Acetonitrile Methanol and Ethanol | |
| Benzoic acid | 1:1 | Cooling | Acetone, Acetonitrile, Methanol, THF | amorphous |
| | | Slurrification | Water, Acetonitrile Methanol and Ethanol | |
| Fumaric acid | 1:1 | Cooling | Acetone, Acetonitrile, Methanol, THF | amorphous |
| | | Slurrification | Water, Acetonitrile Methanol and Ethanol | |
| Maleic acid | 1:1 | Cooling | Acetone, Acetonitrile, Methanol, THF | amorphous |
| | | Slurrification | Water, Acetonitrile Methanol and Ethanol | |
| Methanesulfonic acid | 1:1 | Cooling | Acetone, Acetonitrile, Methanol, THF | amorphous |
| | | Slurrification | Water, Acetonitrile Methanol and Ethanol | |

Noticeable in these experiments was the extreme difficulty to produce crystalline acid salts from (S)-{8-fluoro-2-[4-(3-methoxyphenyl)piperazine-1-yl]-3-[2-methoxy-5-(trifluoro-methyl)phenyl]-3,4-dihydroquinazoline-4-yl}acetic acid, where the first crystallization attempts failed altogether. In the course of further research it has been found, however, that it was possible to obtain crystalline salts both with benzenesulfonic acid and toluenesulfonic acid. The besylate and tosylate salts obtained proved to be easily producible and with a high level of purity. Furthermore, the X-ray diffractograms revealed that these salts crystallize without incorporating solvent molecules.

Exemplary Embodiments

Example 1

Besylate salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid 235.00 g (0.41 mol) of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (Example 6A) are dissolved in 1645 ml of acetone and 16.45 ml of water is added to the resulting mixture. The resulting yellowish solution is filtered and 64.92 g (0.41 mol) of benzenesulfonic acid as a solid is added portion by portion. The resulting solution is heated to about 40° C. and suitable seed crystals are added at this temperature. The resulting solution is cooled down to room temperature under stirring and the resulting suspension is cooled to 0-5° C. and stirred for an additional 2 hours at that temperature. The resulting solid is filtered, washed 2× with acetone (100 ml, 0° C.) and dried at 60° C. to constant weight. This process yields a total of 243.87 g (81.4% of the theoretic quantity) of the target compound.

From the crystalline solid obtained in Example 1, an X-ray powder diffractogram (XRD) was recorded with a Siemens Powder Diffractometer D5000 that is shown in FIG. 1, under the following conditions.

The peak lists for the salt obtained in Example 1 as well as for the salt obtained in Example 2 are shown in Table 2.

Measuring Conditions
  Copper anode (wavelength 1.5418 Å)
  Voltage: 4000 V, Current: 30 mA
  Secondary graphite monochromator,
  variable (theta-dependent) divergence and anti-diffusion shield
  Detector aperture: 0.2 mm
  6×10 mm effective sample surface
  Scanning 0.02° (2 theta), 2 sec.

Example 2

Tosylate salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid 235.00 g (0.41 mol) of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (Example 6A) are dissolved in 1645 ml of acetone and 16.45 ml of water is added to the solution. The resulting yellowish solution is filtered and 78.07 g (0.41 mol) of solid p-toluenesulfonic acid monohydrate are added portion by portion at about 36° C. The solution is cooled down to room temperature under stirring and the resulting suspension is then cooled to 0-5° C. and stirred for an additional 2 hours at that temperature. The solid material is separated, washed 2× with acetone (100 ml, 0° C.) and dried at 60° C. to constant weight. This process yielded a total of 248.11 g (79.3% of the theoretic quantity) of the desired final product.

Figure 2:
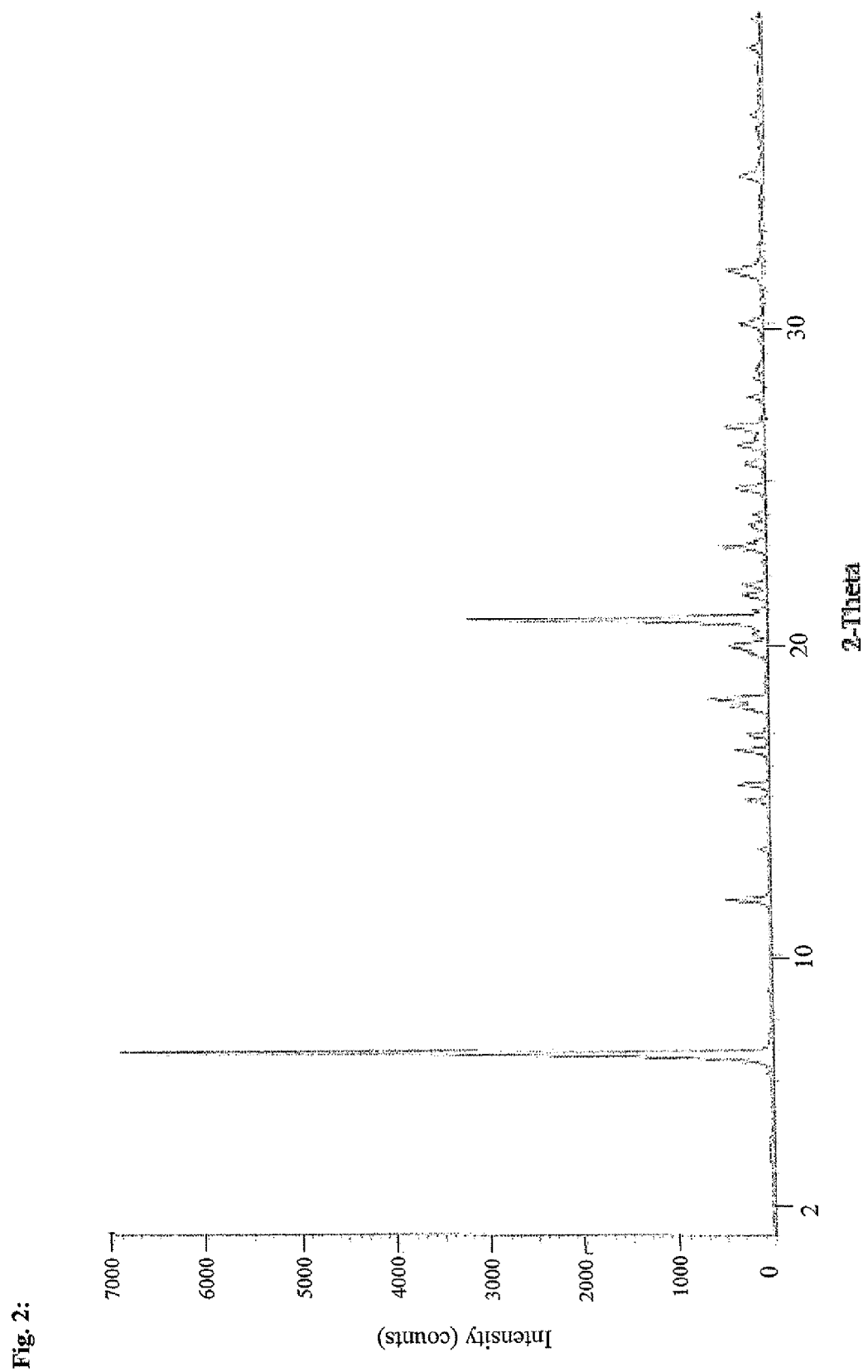

From the crystalline solid material obtained in Example 2 an X-ray powder diffractogram (XRD), shown in FIG. 2, was recorded under the same conditions as for Example 1.

TABLE 2

| 2 theta | |
|---|---|
| Example 1 | Example 2 |
| 6.9 | 6.2 |
| 8.6 | 6.9 |
| 9.1 | 8.8 |
| 10.1 | 11.7 |
| 10.6 | 13.3 |
| 10.9 | 14.8 |
| 11.4 | 15.3 |
| 11.7 | 16.5 |
| 12.6 | 17.0 |
| 12.9 | 17.2 |
| 13.9 | 17.9 |
| 14.2 | 18.1 |
| 14.9 | 18.7 |
| 15.5 | 19.6 |
| 15.8 | 19.8 |
| 16.9 | 20.2 |
| 17.3 | 20.7 |
| 18.2 | 21.0 |
| 18.6 | 21.4 |
| 18.8 | 21.8 |
| 19.1 | 22.5 |
| 20.2 | 23.0 |
| 21.0 | 23.2 |
| 21.3 | 23.7 |
| 21.9 | 24.0 |
| 22.2 | 24.8 |
| 22.8 | 25.6 |
| 23.1 | 26.2 |
| 23.6 | 26.4 |
| 23.9 | 26.7 |
| 24.2 | 27.7 |
| 24.7 | 28.3 |
| 25.5 | 28.6 |
| 25.9 | 29.4 |
| 26.2 | 30.0 |
| 26.5 | 31.8 |
| 26.9 | 34.8 |
| 27.2 | 36.3 |
| 27.9 | 36.7 |
| 28.2 | 38.9 |
| 28.6 | 39.8 |
| 29.0 | |
| 29.4 | |
| 29.9 | |
| 30.6 | |
| 31.1 | |
| 31.5 | |
| 32.6 | |
| 33.1 | |
| 33.7 | |
| 34.4 | |
| 34.9 | |
| 36.6 | |
| 37.5 | |
| 38.1 | |
| 38.9 | |

C.) Exemplary Embodiments

Purity

The compounds according to the invention of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate and S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate were analyzed for chemical purity by means of HPLC (Method 4) described below.

In the context of the present invention the term "chemical purity" describes the amount-of-substance fraction of the above-mentioned salts relative to the total mixture of substances. The undesirable substances are called impurities.

Example aa)

Synthesis of S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate: 235 g (0.41 mol) of said besylate were dissolved in 1645 ml of acetone and 16.45 ml of water. The resulting yellowish solution was filtered and treated portion by portion with 64.92 g (0.41 mol) solid benzenesulfonic acid at about 40° C. The resulting clear solution was cooled down to room temperature under stirring. The suspension thus obtained was further cooled to 0° C.-5° C. under stirring for two hours. The solid portion thereof was isolated, washed twice with acetone (100 ml at 0° C. each) and dried at 60° C. in order to obtain 243.87 g (0.334 mol, 81.4%) crystalline S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate for the purpose of determining the degree of purity.

Example bb)

Synthesis of S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate: 235 g (0.41 mol) of said tosylate were dissolved in 1645 ml of acetone and 16.45 ml of water.

The resulting yellowish solution was filtered and treated portion by portion with 78.07 g (0.41 mol) solid p-toluenesulfonic acid monohydrate at about 36° C. The resulting solution was cooled down to room temperature under stirring. The suspension thus obtained was further cooled to 0° C.-5° C. under stirring for two hours. The solid portion thereof was separated, washed twice with acetone (100 ml at 0° C. each) and dried at 60° C. in order to obtain 248.11 g (0.325 mol, 79.3%) crystalline S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate for the purpose of determining the degree of purity.

Purity Determination

Method 4 (HPLC): Instrument: HP 1050 with UV detection; Column: Phenomenex-Prodigy ODS (3) 100 A, 150 mm×3 mm, 3 µm; Eluent A: (1.36 g $KH_2PO_4$+0.7 ml $H_3PO_4$; 85%)/1 water; Eluent B: Acetonitrile; Gradient: 0 min 20% B, 40 min 45% B, 50 min 80% B; 50 min 80% B, 65 min 80% B, 75 min 20% B; Flow: 0.5 ml/min; Temp.: 55° C.; Injection volume 3 µl, UV detection: 210 nm/BW: 4 nm; Temperature auto-sampler 5° C.

22 mg each of the respective test substances of the salts obtained according to Example aa), Example bb) were dissolved in 50 ml of acetonitrile (c=approx. 0.44 mg/ml). As equivalent reference solutions 22 mg each of S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid were dissolved in 50 ml acetonitrile (c=approx. 0.44 mg/ml).

As reference solutions of the known impurities 5 mg each of di-p-toluoyl-D-tartaric acid and/or S-quinazoline piperazine, quinazoline ethyl ester and quinazoline dipiperazine were mixed separately with acetonitrile to 50 ml. 1 ml each of the reference solutions for known impurities was then dissolved separately in 10 ml of acetonitrile (c=approx. 0.44 mg/ml).

Furthermore, 10 ml each of the reference solutions of S(+)-{-8-fluoro-2-[4-(3-methoxyphenyl)piperazine-1-yl]-3-[2-methoxy-5-(trifluoromethyl)phenyl]-3,4-dihydroquinazoline-4-yl}acetic acid were mixed with 1 ml each of the reference solution for the above-mentioned impurities.

The evaluation of the HPLC analysis was conducted based on the so-called relative area percent method which takes the respective response factors (RF) (RF=1.02 for quinazoline piperazine and 0.81 for quinazoline dipiperazine) into account.

Figure 4:
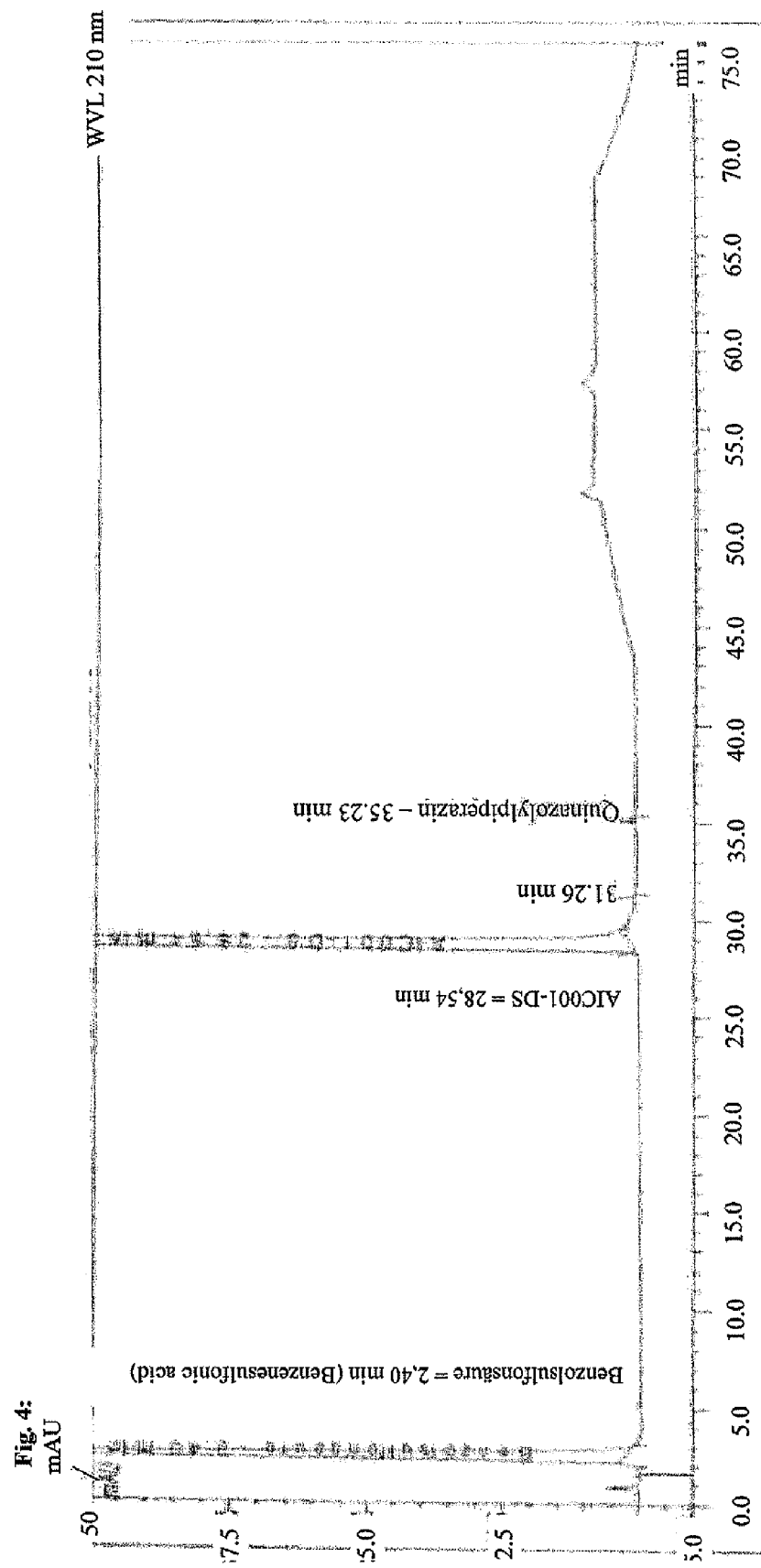
FIG. 4 an HPLC purity chromatogram of S(+){8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate.

The results for S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid besylate are shown in FIGS. 3 and 4 and for S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid tosylate in FIGS. 5 and 6.

D.) Pharmaceutical Composition

Tablet:
Composition:
128 mg of the salt from Example 1 (corresponding to 100 mg of the active ingredient), 50 mg lactose (monohydrate), 50 mg corn starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm.
Production:
The mixture consisting of active ingredient, lactose and starch is granulated with a 5% solution (m/m) of PVP in water. After drying, the granulate is mixed with the magnesium stearate for 5 min. and the resulting mixture is pressed with a conventional tablet press (see tablet format above). A pressing force of 15 kN is used as reference value for the pressing process.

The invention claimed is:

1. A method for purifying {8-fluoro-2-[4-(3-methoxyphenyl)piperazine-1-yl]-3-[2-methoxy-5-(trifluoromethyl)phenyl]-3,4-dihydroquinazoline-4-yl}acetic acid using the following steps:
   1.) Reacting {8-fluoro-2-[4-(3-methoxyphenyl)piperazine-1-yl]-3-[2-methoxy-5-(trifluoromethyl)phenyl]-3,4-dihydroquinazoline-4-yl}acetic acid in a solvent with benzenesulfonic acid or toluenesulfonic acid to obtain a crystalline salt,
   2.) Isolating the salt obtained in step 1.),
   3.) Treating the isolated salt obtained in step 2.) with a buffer solution at a pH in the range of 5 to 7 to release a zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, and
   4). Isolating the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid obtained in step 3.).

2. A method according to claim 1, wherein the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid comprises less than 0.1% impurities.

3. A method according to claim 1, wherein the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid comprises less than 0.08% impurities.

4. A method according to claim 1, wherein the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid comprises less than 0.05% impurities.

5. The method according to claim 1, wherein the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is suitable for preparation of the crystalline besylate salt of {8-fluoro-2-[4-(3-methoxyphenyl)piperazine-1-yl]-3-[2-methoxy-5-(trifluoromethyl) phenyl]-3,4-dihydroquinazoline-4-yl}acetic acid, the crystalline tosylate salt of {8-fluoro-2-[4-(3-methoxyphenyl) piperazine-1-yl]-3-[2-methoxy-5-(trifluoromethyl)phenyl]-3,4-dihydroquinazoline-4-yl}acetic acid, or solvates thereof.

6. A method according to claim 5, wherein a salt or solvate prepared from the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, is suitable for use in a method of treatment and/or prophylaxis of human cytomegalovirus (HCMV) infections or infections with another representative of the herpes viridae group.

7. The method according to claim 6, wherein the said infection of the herpes viridae group is human cytomegalovirus (HCMV).

8. A method according to claim 5, wherein a salt or solvate prepared from the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, is suitable for combination with at least one pharmaceutically acceptable excipient for use in a method of treatment and/or prophylaxis of human cytomegalovirus (HCMV) infections or infections with another representative of the herpes viridae group.

9. A method for purifying {8-fluoro-2-[4-(3-methoxyphenyl)piperazine-1-yl]-3-[2-methoxy-5-(trifluoromethyl)phenyl]-3,4- dihydroquinazoline-4-yl}acetic acid using the following steps:
 1.) reacting {8-fluoro-2-[4-(3-methoxyphenyl)piperazine-1-yl]-3-[2-methoxy-5-(trifluoromethyl)phenyl]-3,4- dihydroquinazoline-4-yl}acetic acid in a solvent with benzenesulfonic acid or toluenesulfonic acid,
 2.) cooling the reaction from step 1) to initiate the crystallization of the salt obtained in step 1.),
 3.) treating the isolated salt obtained in step 2.) with a buffer to release a zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, and
 4). isolating the zwitterionic form of {8-fluoro-2-[4-(3-methoxyphenyl)piperazine-1-yl]-3-[2-methoxy-5-(trifluoromethyl)phenyl]-3,4-dihydroquinazoline-4-yl}acetic acid obtained in step 3.).

* * * * *